United States Patent
Oberboersch et al.

(10) Patent No.: US 7,345,055 B2
(45) Date of Patent: *Mar. 18, 2008

(54) SUBSTITUTED C-IMIDAZO [1,2-α] PYRIDIN-3-YL-METHYLAMINES

(75) Inventors: Stefan Oberboersch, Aachen (DE); Bernd Sundermann, Aachen (DE); Corinna Sundermann, Aachen (DE); Hagen-Heinrich Hennies, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 116 days.

This patent is subject to a terminal disclaimer.

(21) Appl. No.: 11/101,471

(22) Filed: Apr. 8, 2005

(65) Prior Publication Data
US 2005/0239823 A1    Oct. 27, 2005

Related U.S. Application Data

(63) Continuation of application No. PCT/EP03/11079, filed on Oct. 7, 2003.

(30) Foreign Application Priority Data
Oct. 10, 2002   (DE)  ................... 102 47 269

(51) Int. Cl.
  *A61K 31/44*  (2006.01)
  *C07D 471/02*  (2006.01)
  *C07D 491/02*  (2006.01)
  *C07D 498/02*  (2006.01)
  *C07D 513/02*  (2006.01)

(52) U.S. Cl. .................. 514/300; 546/121

(58) Field of Classification Search .......... 546/121; 514/300
See application file for complete search history.

(56) References Cited

U.S. PATENT DOCUMENTS

| 4,650,796 A | 3/1987 | George et al. |
| 5,047,411 A * | 9/1991 | Takasugi et al. ............ 514/300 |
| 2005/0239822 A1* | 10/2005 | Hennies et al. ............ 514/303 |

FOREIGN PATENT DOCUMENTS

EP   0 172 096 A   2/1986

OTHER PUBLICATIONS

Almirante et al., Bollettino Chimico Farmaceutico, 1966, "Syntheses and reactions of imidazoles", vol. 105, pp. 32-44.*
Freshney et al., Culture of animal cells, "a manual of basic techniques"1983, pp. 1-6.*
Dermer et al., Bio/Technology, "another anniversary for the war on cancer", 1994, vol. 12, p. 320.*
Katsura et al., Chemical & Pharmaceutical Bulletin, "Studies on antiulcer drugs. III. Synthesis and antiulcer activities of imidazo[1,2-a]pyridinylethyl-benzoxazoles and related compounds. A novel class of Histamine H2-receptor antagonists", 1992, vol. 40,pp. 1424-1438.*
Almirante et al., Bollettino Chimico Farmaceutico, "Imidazole derivatives. VI. synthesis and pharmacological activity of nitrogen-containing derivatives of imidazo[1,2-a]pyridine", 1971, vol. 110, pp. 322-329.*
Almirante et al., Sintesi E Reazioni Di Derivati Dell'lmidazolo, Bol. Chim. Farm, vol. 105, 19966, pp. 32-44.
International Search Report.

* cited by examiner

*Primary Examiner*—Margaret D. Seaman
*Assistant Examiner*—Niloofar Rahmani
(74) *Attorney, Agent, or Firm*—Crowell & Moring LLP

(57) ABSTRACT

Novel C-imidazo[1,2-α]pyridin-3-yl-methylamine compounds corresponding to formula I, wherein $R^1$-$R^6$ have the meanings provided in the description. Pharmaceutical compositions containing these compounds are also provided, as well as methods of using these compounds for treating or inhibiting various illnesses or other conditions.

18 Claims, No Drawings

SUBSTITUTED C-IMIDAZO [1,2-α] PYRIDIN-3-YL-METHYLAMINES

CROSS REFERENCE TO RELATED APPLICATIONS

This application is a continuation of international patent application no. PCT/EP2003/011079, filed Oct. 7, 2003, designating the United States of America, and published in English as WO 2004/035578 A1, the entire disclosure of which is incorporated herein by reference. Priority is claimed based on German patent application no. 102 47 269.6, filed Oct. 10, 2002.

FIELD OF THE INVENTION

The present invention relates to substituted C-imidazo[1,2-α]pyridin-3-yl-methylamines as well as their physiologically compatible salts, processes for their preparation, pharmaceutical formulations containing these compounds and the use of substituted C-imidazo[1,2-α]pyridin-3-yl-methylamines for the preparation of pharmaceutical formulations and in methods of treating/inhibiting disease.

BACKGROUND OF THE INVENTION

Nitrogen monoxide (NO) regulates numerous physiological processes, inter alia neurotransmission, the relaxation and proliferation of smooth musculature, the adhesion and aggregation of thrombocytes, as well as tissue damage and inflammation. On account of the large number of important functions nitrogen monoxide is implicated in a whole range of medical conditions, described for example in L. J. Ignarro, Angew. Chem. (1999), 111, pp. 2002-2013 and in F. Murad, Angew. Chem. Int. Ed. (1999), 111, pp. 1976-1989. The enzyme responsible for the physiological formation of nitrogen monoxide, namely nitrogen monoxide synthase (NO synthase), accordingly plays an important role in the therapeutic treatment of these medical conditions. Up to now three different isomeric forms of NO synthase have been identified, namely the two constitutive forms nNO synthase and eNO synthase, as well as the inducible form iNO synthase (A. J. Hobbs, A. Higgs, S. Moncada, Annu. Rev. Pharmacol. Toxicol. (1999), 39, pp. 191-220; I. C. Green, P.-E. Chabrier, DDT (1999), 4, pp. 47-49; P.-E. Chabrier et al., Cell. Mol. Life Sci. (1999), 55, pp. 1029-1035).

The inhibition of NO synthase opens up new approaches for the treatment of various medical conditions in which nitrogen monoxide is implicated (A. J. Hobbs et al., Annu. Rev. Pharmacol. Toxicol. (1999), 39, pp. 191-220; I. C. Green, P.-E. Chabrier, DDT (1999), 4, pp. 47-49; P.-E. Chabrier et al., Cell. Mol. Life Sci. (1999), 55, pp. 1029-1035), such as for example migraine (L. L. Thomsen, J. Olesen, Clinical Neuroscience (1998), 5, pp. 28-33; L. H. Lassen et al., The Lancet (1997), 349,401-402), septic shock, neurodegenerative diseases such as multiple sclerosis, Parkinson's disease, Alzheimer's disease or Huntington's disease, inflammatory conditions, inflammation pain, cerebral ischemia, diabetes, meningitis and arteriosclerosis. In addition the inhibition of NO synthase may have an effect on wound healing, on tumours and on angiogenesis, as well as producing a non-specific immunity to microorganisms (A. J. Hobbs et al., Annu. Rev. Pharmacol. Toxicol. (1999), 39, pp. 191-220).

Hitherto known active substances that inhibit NO synthase include, apart from L-NMMA and L-NAME—i.e. analogues of L-arginine, from which nitrogen monoxide and citrullin are formed in vivo with the involvement of NO synthase—inter alia S-methyl-L-citrullin, aminoguanidine, S-methyliso-urea, 7-nitroindazole and 2-mercaptoethylguanidine (A. J. Hobbs et al., Annu. Rev. Pharmacol. Toxicol. (1999), 39, pp. 191-220).

An object of the present invention was accordingly to provide new substances that have an inhibitory effect on nitrogen monoxide synthase. In particular the pharmaceutical formulations should be suitable for treating migraine, septic shock, neurodegenerative diseases such as multiple sclerosis, Parkinson's disease, Alzheimer's disease or Huntington's disease, inflammatory conditions, inflammation pain, cerebral ischemia, diabetes, meningitis, arteriosclerosis, cancers, fungal diseases or wound healing.

It has now been found that substituted C-imidazo[1,2-α]pyridin-3-yl-methylamines of the following general formula I act as inhibitors of nitrogen monoxide synthase and are particularly suitable for the treatment of migraine, septic shock, neurodegenerative diseases such as multiple sclerosis, Parkinson's disease, Alzheimer's disease or Huntington's disease, inflammatory conditions, inflammation pain, cerebral ischemia, diabetes, meningitis, arteriosclerosis, cancers, fungal diseases or wound healing.

The present invention accordingly provides substituted C-imidazo[1,2-α]pyridin-3-yl-methylamines of the general formula I,

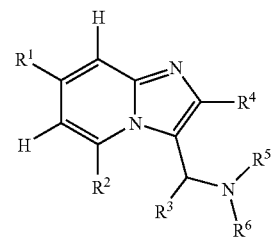

wherein in each case $R^1$ denotes OH, SH, $NH_2$, $NHCH_3$, $N(CH_3)_2$, $CH_3$, $CH_2Cl$, $CH_2F$, $CHF_2$, $CF_3$, $OCH_3$, $OCH_2Cl$, $OCH_2F$, $OCHF_2$, $OCF_3$, $SCH_3$, $SCF_3$, $C_2H_5$, $CHClCH_3$, $CH_2CH_2Cl$, $CHFCH_3$, $CH_2CH_2F$, $CH_2CHF_2$, $CH_2CF_3$, $OC_2H_5$, COOH, $CH_2OH$, $CHOHCH_3$, $CH_2CH_2OH$, CN, $NO_2$, F, Br, I or Cl, $R^2$ denotes H or $CH_3$, $R^3$ denotes H; $C_{1-6}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched; $C_{3-8}$-cycloalkyl, in each case singly or multiply substituted or unsubstituted, singly unsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted or unsubstituted; or aryl or heteroaryl, in each case substituted or unsubstituted; or COOR$^{10}$, R$^4$ denotes H; C$_{1-12}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, heptyl, octyl, nonyl, decyl, undecyl, dodecyl, in each case singly or multiply substituted or unsubstituted, branched or unbranched, or in each case optionally singly or multiply substituted or unsubstituted, branched or unbranched; C$_{3-8}$-cycloalkyl, in each case singly or multiply substituted or unsubstituted, singly unsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted or unsubstituted; or a radical according to formula II,

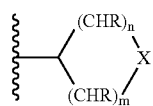

wherein in each case
n denotes a number between 0 and 6,
m denotes a number between 0 and 6, $1 \leq m+n \leq 6$,
x denotes O, S, SO, SO$_2$ or NR$^7$,
R independently of one another denotes H, F, Br, I, Cl, OH, SH, NH$_2$, NO$_2$, CH$_3$, C$_2$H$_5$, OCH$_3$, OC$_2$H$_5$, OCF$_3$, R$^5$ denotes H; C$_{1-6}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched; or C$_{3-8}$-cycloalkyl, in each case singly or multiply substituted or unsubstituted, singly unsaturated or saturated; cyclopropyl, cyclobutyl, cyclopentyl, cyclohexyl, cycloheptyl, cyclooctyl, 2-methylcyclo-propyl, cyclopropylmethyl, 2-methylcyclobutyl, 3-methylcyclobutyl, cyclobutylmethyl, in each case substituted or unsubstituted;

R$^6$ denotes H; C$_{1-6}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched; or C$_{3-8}$-cycloalkyl, in each case singly or multiply substituted or unsubstituted, singly unsaturated or saturated; cyclopropyl, cyclobutyl, cyclopentyl, cyclohexyl, cycloheptyl, cyclooctyl, 2-methylcyclo-propyl, cyclopropylmethyl, 2-methylcyclobutyl, 3-methylcyclobutyl, cyclobutylmethyl, in each case substituted or unsubstituted; or aryl, heteroaryl, C$_{1-4}$-alkyl aryl or C$_{1-4}$-alkyl heteroaryl; unsubstituted or singly or multiply substituted;

or the radicals R$^5$ and R$^6$ together form a ring and denote CH$_2$CH$_2$OCH$_2$CH$_2$, CH$_2$CH$_2$NR$^{11}$CH$_2$CH$_2$ or (CH$_2$)$_{3-6}$, R$^7$ denotes H, a C$_{1-6}$-alkyl radical, preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, 1-ethylpropyl or hexyl, a C$_{3-8}$-cycloalkyl radical, preferably cyclopropyl, 2-methylcyclopropyl, cyclopropylmethyl, cyclobutyl, 2-methylcyclobutyl, 3-methylcyclobutyl, cyclobutylmethyl, cyclopentyl, cyclohexyl or cyclooctyl, an acyl radical C(O)R$^8$ or a sulfonyl radical S(O$_2$)R$^9$, R$^8$ denotes H, a C$_{1-6}$-alkyl radical or an aryl radical,
R$^9$ denotes H, a C$_{1-6}$-alkyl radical or an aryl radical,
R$^{10}$ denotes H, a C$_{1-6}$-alkyl radical or an aryl radical,
R$^{11}$ denotes H, C$_{1-6}$-alkyl or C$_{3-8}$-cycloalkyl, aryl or heteroaryl, aryl or heteroaryl bonded via C$_{1-3}$-alkylene, acyl C(O)R$^{12}$ or sulfonyl S(O$_2$)R$^{13}$,
R$^{12}$ denotes H, a C$_{1-6}$-alkyl radical or an aryl radical,
R$^{13}$ denotes H, a C$_{1-6}$-alkyl radical or an aryl radical, optionally in the form of their racemates, their pure stereoisomers, in particular enantiomers or diastereomers, or in the form of mixtures of the stereoisomers, in particular the enantiomers or diastereomers, in an arbitrary mixture ratio;

in the prepared form or in the form of their acids or their bases or in the form of their salts, in particular physiologically compatible salts, or in the form of their solvates, in particular hydrates;

with the proviso that the following compounds:

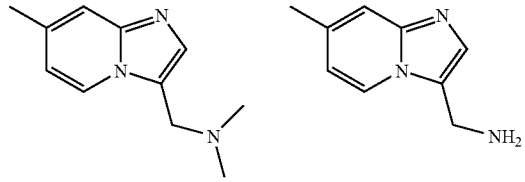

are excluded from protection.

The expression "C$_{1-12}$-alkyl radical" includes within the context of the present invention acyclic saturated or unsaturated hydrocarbon radicals that may be branched or straight-chain as well as unsubstituted or at least singly substituted, with 1 to 12 carbon atoms. This means that, apart from C$_{1-12}$-alkanylenes, also C$_{2-12}$-alkenyls and C$_{1-12}$-alkinyls are included, in which the alkenyls contain at least one carbon-carbon double bond and the alkinyls contain at least one carbon-carbon triple bond. Preferably the C$_{1-12}$-alkyl radical is selected from the group comprising methyl, ethyl, n-propyl, 2-propyl, n-butyl, isobutyl, sec.-butyl, tert.-butyl, n-pentyl, isopentyl, neopentyl, n-hexyl, 2-hexyl, n-octyl, ethenyl(vinyl), ethinyl, propenyl(—CH$_2$CH═CH$_2$, —CH═CH—CH$_3$, —C(═CH$_2$)—CH$_3$), propinyl(—CH—C≡CH, —C≡C—CH$_3$), butenyl, butinyl, pentenyl, pentinyl, hexenyl, hexinyl, octenyl and octinyl.

Where the C$_{1-12}$-alkyl radical is present singly or multiply substituted, then one or more hydrogen atoms is/are preferably replaced by a substituent selected from the group comprising F, Cl, Br, I, CN, NH₂, NH-alkyl, NH-aryl, NH-heteroaryl, NH-alkylaryl, NH-alkylheteroaryl, NH-heterocyclyl, NH-alkyl-OH, N(alkyl)₂, N(alkylaryl)₂, N(alkylheteroaryl)₂, N(heterocyclyl)₂, N(alkyl-OH)₂, NO, NO₂, SH, S-alkyl, S-aryl, S-heteroaryl, S-alkylaryl, S-alkylheteroaryl, S-heterocyclyl, S-alkyl-OH, S-alkyl-SH, OH, O-alkyl, O-aryl, O-heteroaryl, O-alkylaryl, O-alkyl-heteroaryl, O-heterocyclyl, O-alkyl-OH, CHO, C(=O)C₁₋₆-alkyl, C(=S)C₁₋₆-alkyl, C(=O)aryl, C(=S)aryl, C(=O) C₁₋₆-alkylaryl,

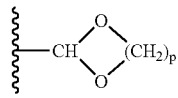

where p=1, 2 or 3, C(=S)C₁₋₆-alkylaryl, C(=O)-heteroaryl, C(=S)-heteroaryl, C(=O)-heterocyclyl, C(=S)-heterocyclyl, CO₂H, CO₂-alkyl, CO₂-alkylaryl, C(=O)NH₂, C(=O)NH-alkyl, C(=O)NHaryl, C(=O)NH-heterocyclyl, C(=O)N(Alkyl)₂, C(=O)N(alkylaryl)₂, C(=O)N(alkylheteroaryl)₂, C(=O)N(heterocyclyl)₂, SO-alkyl, SO₂-alkyl, SO₂NH₂, SO₃H, cycloalkyl, aryl, heteroaryl and heterocyclyl, in which connection multiply substituted C₁₋₆-alkyl radicals are understood to be those radicals that are multiply substituted, for example doubly or triply substituted, either on different atoms or on the same atom of the C₁₋₆-alkyl radical, for example triply substituted on the same carbon atom as in the case of CF₃ or —CH₂CF₃, or on different atoms as in the case of —CH(OH)—CH=CH—CHCl₂. The multiple substitution may be carried out with the same or with different substituents. Where the substituent itself contains an alkyl group, this is preferably selected from the group comprising methyl, ethyl, CH₂—OH and CF₃.

The expression "C₃₋₈-cycloalkyl radical" includes, for the purposes of the present invention, cyclic hydrocarbons with 3 to 8 carbon atoms, which may be saturated or unsaturated, unsubstituted or at least singly substituted, in which the bonding between the cycloalkyl radical and the base skeleton of the general formula I may be effected via any arbitrary ring member of the cycloalkyl radical. Preferably the C₃₋₈-cycloalkyl radical is selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl. Particularly preferably the C₃₋₈-cycloalkyl radical is a cyclohexyl radical.

The expression "aryl radical" denotes within the context of the present invention aromatic hydrocarbons that may also be condensed with further saturated, at least partially unsaturated or aromatic ring systems, in which the bonding of the aryl radical to the base skeleton of the general formula I may be effected via any arbitrary ring member of the aryl radical. Where the aryl radical contains more than one substituent, these may be identical or different and may be present in any arbitrary and possible position on the aryl radical. Preferably the aryl radical is selected from the group comprising unsubstituted or at least singly substituted phenyl, anthracenyl, 1-naphthyl and 2-naphthyl. Particularly preferably the aryl radical is selected from the group comprising phenyl, 3-hydroxyphenyl, 3-methoxyphenyl, 2,3-dihydroxyphenyl, 2,3-dimethoxyphenyl and 1-naphthyl.

Where the C₃₋₈-cycloalkyl or the aryl radical is singly or multiply substituted, this is understood hereinafter to denote preferably single or multiple substitution, e.g. disubstitution, trisubstitution or tetrasubstitution of one or more hydrogen atoms of the ring system by a substituent selected from the group comprising F, Cl, Br, I, CN, NH₂, NH-alkyl, NH-aryl, NH-heteroaryl, NH-alkylaryl, NH-alkylheteroaryl, NH-heterocyclyl, NH-alkyl-OH, N(alkyl)₂, N(alkylaryl)₂, N(alkylheteroaryl)₂, N(heterocyclyl)₂, N(alkyl-OH)₂, NO, NO₂, SH, S-alkyl, S-cycloalkyl, S-aryl, S-heteroaryl, S-alkylaryl, S-alkylheteroaryl, S-heterocyclyl, S-alkyl-OH, S-alkyl-SH, OH, O-alkyl, O-cycloalkyl, O-aryl, O-heteroaryl, O-alkylaryl, O-alkyl-heteroaryl, O-heterocyclyl, O-alkyl-OH, CHO, C(=O)C₁₋₆-alkyl, C(=S)C₁₋₆-alkyl, C(=O)aryl, C(=S)aryl, C(=O)—C₁₋₆-alkylaryl,

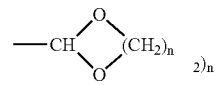

where n=1, 2 or 3, C(=S)C₁₋₆-alkylaryl, C(=O)-heteroaryl, C(=S)-heteroaryl, C(=O)-heterocyclyl, C(=S)-heterocyclyl, CO₂H, CO₂-alkyl, CO₂-alkylaryl, C(=O)NH₂, C(=O)NH-alkyl, C(=O)NHaryl, C(=O)NH-heterocyclyl, C(=O)N(Alkyl)₂, C(=O)N(alkylaryl)₂, C(=O)N(alkylheteroaryl)₂, C(=O)N(heterocyclyl)₂, S(O)-alkyl, S(O)-aryl, SO₂-alkyl, SO2-aryl, SO₂NH₂, SO₃H, CF₃, =O, =S; alkyl, cycloalkyl, aryl, heteroaryl and heterocyclyl, in which connection a substituent may itself optionally be substituted. The multiple substitution is carried out with the same or different substituents. For "aryl radicals" particularly preferred substituents are selected from the group comprising F, CF₃, OH and O—CH₃. For "cycloalkyl radicals" particularly preferred substituents are CO₂H or CO₂ethyl.

The expression "heteroaryl" within the context of the present invention denotes a 5-, 6- or 7-membered cyclic aromatic radical that comprises at least 1, optionally also 2, 3, 4 or 5 heteroatoms, in which the heteroatoms may be identical or different and in which the bonding to the base skeleton of the general formula I may take place via any arbitrary and possible ring member of the heteroaryl radical. Where the heteroaryl radical contains more than one substituent, these heteroaryl substituents may be identical or different and may be present in any arbitrary and possible position of the heteroaryl radical. The heterocycle may also be condensed with further saturated, at least partially unsaturated or aromatic ring systems. Preferred heteroatoms are selected from the group comprising nitrogen, oxygen and sulfur. Preferably the heteroaryl radical is selected from the group comprising unsubstituted or at least singly substituted pyrrolyl, furyl, thienyl, pyrazolyl, imidazolyl, pyridinyl, pyridazinyl, pyrimidinyl, pyrazinyl, pyranyl, indolyl, indazolyl, purinyl, pyrimidinyl, indolizinyl, quinolinyl, isoquinolinyl, quinazolinyl, carbazolyl, phenazinyl and phenothiazinyl. Particularly preferred heteroaryl radicals are selected from the group comprising pyridin-2-yl, pyridin-3-yl, furan-2-yl, furan-3-yl, 5-hydroxymethylene-furan-2-yl, 5-nitrofuran-2-yl, 5-[1,3]-dioxolanefuran-2-yl, 5-carboxylic acid furan-2-yl, thien-2-yl (2-thiophene), thien-3-yl(3-thiophene) and 5-carboxylic acid 2-thiophene (5-carboxylic acid thien-2-yl).

The expression "heterocyclyl" includes in the context of the present invention a 3-, 4-, 5-, 6- or 7-membered cyclic organic radical that contains at least 1, optionally also 2, 3, 4 or 5 heteroatoms in the ring system, in which the heteroatoms may be identical or different and the cyclic radical is saturated or unsaturated but is not aromatic, and may be unsubstituted or at least singly substituted. The bonding of the heterocyclyl radical to the base skeleton of the general formula I may take place via any arbitrary ring member of the heterocyclyl radical. The heterocyclyl radical may also be part of a bicyclic or polycyclic system. Preferred heteroatoms are selected from the group comprising nitrogen, oxygen and sulfur. Preferably the $C_{3-7}$-heterocyclyl radical is selected from the group comprising tetrahydrofuryl, tetrahydropyranyl, pyrrolidinyl, piperidinyl, piperazinyl and morpholinyl.

Where the compounds according to the invention of the general formula I or their physiologically compatible salts contain at least one asymmetry centre, they may be present in the form of their racemates, their pure enantiomers, their pure diastereomers, or in the form of a mixture of at least two of the aforementioned stereoisomers. Likewise, the substituted C-imidazo[1,2-α]pyridin-3-yl-methylamines of the general formula I may also be present in the form of mixtures of their enantiomers or diastereomers. These mixtures may contain the respective stereoisomers in any arbitrary mixture ratio. Chiral substituted C-imidazo[1,2-α] pyridin-3-yl-methylamines of the general formula I are preferably used in enantiomer-pure form.

Within the context of the present invention alkyl and cycloalkyl radicals are also understood to mean saturated and unsaturated (but not aromatic), branched, unbranched and cyclic hydrocarbons, which may be unsubstituted or singly or multiply substituted. In this connection $C_{1-2}$-alkyl denotes C1- or C2-alkyl, $C_{1-3}$-alkyl denotes C1-, C2- or C3-alkyl, $C_{1-4}$-alkyl denotes C1-, C2-, C3- or C4-alkyl, $C_{1-5}$-alkyl denotes C1-, C2-, C3-, C4- or C5-alkyl, $C_{1-6}$-alkyl denotes C1-, C2-, C3-, C4-, C5- or C6-alkyl, $C_{1-7}$-alkyl denotes C1-, C2-, C3-, C4-, C5-, C6- or C7-alkyl, $C_{1-8}$-alkyl denotes C1-, C2-, C3-, C4-, C5-, C6-, C7- or C8-alkyl, $C_{1-10}$-alkyl denotes C1-, C2-, C3-, C4-, C5-, C6-, C7-, C8,- C9- or $C_{10}$-alkyl and $C_{1-18}$-alkyl denotes C1-, C2-, C3-, C4-, C5-, C6-, C7-, C8,- C9-, C10-, C11-, C12-, C13-, C14-, C15-, C16-, C17- or $C_{1-8}$-alkyl. In addition $C_{3-4}$-cycloalkyl denotes C3- or C4-cycloalkyl, $C_{3-5}$-cycloalkyl denotes C3-, C4- or C5-cycloalkyl, $C_{3-6}$-cycloalkyl denotes C3-, C4-, C5- or C6-cycloalkyl, $C_{3-7}$-cycloalkyl denotes C3-, C4-, C5-, C6- or C7-cycloalkyl, $C_{3-8}$-cycloalkyl denotes C3-, C4-, C5-, C6-, C7- or C8-cycloalkyl, $C_{4-5}$-cycloalkyl denotes C4- or C5-Cycloalkyl, $C_{4-6}$-cycloalkyl denotes C4-, C5- or C6-cycloalkyl, $C_{4-7}$-cycloalkyl denotes C4-, C5-, C6- or C7-cycloalkyl, $C_{5-6}$-cycloalkyl denotes C5- or C6-cycloalkyl and $C_{5-7}$-cycloalkyl denotes C5-, C6- or C7-cycloalkyl. With regard to cycloalkyl the term also includes saturated cycloalkyls in which 1 or 2 carbon atoms are replaced by a heteroatom S, N or O. The term cycloalkyl includes however in particular also singly or multiply, preferably singly, unsaturated cycloalkyls without a heteroatom in the ring, provided that the cycloalkyl does not form an aromatic system. Preferably the alkyl and cycloalkyl radicals are methyl, ethyl, vinyl(ethenyl), propyl, allyl(2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentyl-methyl, cyclohexyl, cycloheptyl, cyclooctyl, but also adamantyl, $CHF_2$, $CF_3$ or $CH_2OH$ as well as pyrazolinone, oxopyrazolinone, [1,4]dioxane or dioxolane.

At the same time, in connection with alkyl and cycloalkyl—unless expressly defined otherwise—the term "substituted" within the context of the present invention is also understood to mean the substitution of at least one (optionally also several) hydrogen atom(s) by F, Cl, Br, I, $NH_2$, SH or OH, in which "multiply substituted" and "substituted" in the case of multiple substitution is understood to mean that the substitution takes place multiply with the same or different substituents, on different as well as at the same atoms, for example triply on the same C atom, as in the case of $CF_3$, or at different sites, as in the case of —CH(OH)—CH=CH—$CHCl_2$. Particularly preferred substituents in this connection are F, Cl and OH. With regard to cycloalkyl, the hydrogen atom may also be replaced by $OC_{1-3}$-alkyl or $C_{1-3}$-alkyl (in each case singly or multiply substituted or unsubstituted), in particular by methyl, ethyl, n-propyl, i-propyl, $CF_3$, methoxy or ethoxy.

The term $(CH_2)_{3-6}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—, $(CH_2)_{1-4}$ is understood to denote —$CH_2$—, —$CH_2$—$CH_2$—, —$CH_2$—$CH_2$—$CH_2$— and —$CH_2$—$CH_2$—$CH_2$—$CH_2$-, $(CH_2)_{4-5}$ is understood to denote —$CH_2$—$CH_2$—$CH_2$—$CH_2$— and —$CH_2$—$CH_2$—$CH_2$—$CH_2$—$CH_2$—, etc.

The term aryl radical is also understood to mean ring systems with at least one aromatic ring but without heteroatoms in even only one of the rings. Examples are phenyl, naphthyl, fluoranthenyl, fluorenyl, tetralinyl or indanyl, in particular 9H-fluorenyl or anthracenyl radicals, which may be unsubstituted or singly or multiply substituted.

The term heteroaryl radical is also understood to mean heterocyclic ring systems with at least one unsaturated ring, which may contain one or more heteroatoms from the group comprising nitrogen, oxygen and/or sulfur, and may also be singly or multiply substituted. Examples that may be given from the group comprising heteroaryls are furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole, indole and quinazoline.

In connection with aryl and heteroaryl the term substituted is also understood to mean the substitution of the aryl or heteroaryl with $R^{23}$, $OR^{23}$ or a halogen, preferably F and/or Cl, a $CF_3$, a CN, an $NO_2$, an $NR^{24}R^{25}$, a $C_{1-6}$-alkyl, (saturated), a $C_{1-6}$-alkoxy, a $C_{3-8}$-cycloalkoxy, a $C_{3-8}$-cycloalkyl or a $C_{2-6}$-alkylene.

In this connection the radical $R^{23}$ denotes H, a $C_{1-10}$-alkyl, preferably a $C_{1-6}$-alkyl radical, an aryl or heteroaryl radical or an aryl or heteroaryl radical bonded via a $C_{1-3}$-alkylene group, in which connection these aryl and heteroaryl radicals may not themselves be substituted by aryl or heteroaryl radicals.

The radicals $R^{24}$ and $R^{25}$, which are identical or different, denote H, a $C_{1-10}$-alkyl, preferably a $C_{1-6}$-alkyl radical, an aryl, a heteroaryl or an aryl or heteroaryl radical bonded via a $C_{1-3}$-alkylene group, in which these aryl and heteroaryl radicals may not themselves be substituted by aryl or heteroaryl radicals, or the radicals $R^{24}$ and $R^{25}$ together denote $CH_2CH_2OCH_2CH_2$, $CH_2CH_2NR^{26}CH_2CH_2$ or $(CH_2)_{3-6}$, and the radical $R^{26}$ denotes H, a $C_{1-10}$-alkyl, preferably a $C_{1-6}$-alkyl radical, an aryl or heteroaryl radical, or denotes an aryl or heteroaryl radical bonded via a $C_{1-3}$-alkylene group, in which these aryl and heteroaryl radicals may not themselves be substituted by aryl or heteroaryl radicals.

The term salt is understand within the context of the present invention to mean any form of the active constituent according to the invention in which it adopts an ionic form or is charged and is coupled to a counterion (a cation or anion), and is present in solution. The term salt is also understood to include complexes of the active constituent with other molecules and ions, in particular complexes that are complexed via ionic interactions.

The term physiologically compatible salt (in particular with cations or bases) is understood within the context of the present invention to mean salts of at least one of the compounds according to the invention—generally a (deprotonated) acid—as anion with at least one, preferably inorganic, cation, that is/are physiologically compatible, especially when used in humans and/or mammals. Particularly preferred are the salts of alkali metals and alkaline earth metals, and also salts with $NH_4^+$, but in particular (mono) or (di) sodium, (mono) or (di) potassium, magnesium or calcium salts.

The term physiologically compatible salt (especially with anions or acids) is understood within the context of the present invention to mean further salts of at least one of the compounds according to the invention—generally protonated for example on the nitrogen atom—as cation with at least one anion, that is/are physiologically compatible, in particular when used in humans and/or mammals. In particular the term physiologically compatible salt is understood within the context of the present invention to mean the salt formed with a physiologically compatible acid, namely salts of the respective active constituent with inorganic or organic acids that are physiologically compatible, especially when used in humans and/or mammals. Examples of physiologically compatible salts of specific acids are salts of: hydrochloric acid, hydrobromic acid, sulfuric acid, methansulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro1b6-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-liponic acid, acetylglycine, acetylsalicylic acid, hippuric acid and/or aspartic acid. The hydrochloride salt is particularly preferred.

Suitable salts within the context of the present invention and in each described use and in each of the described pharmaceutical formulations are salts of the respective active constituent with inorganic or organic acids and/or a sugar substitute such as saccharine, cyclamate or acesulfame. However, the hydrochloride is particularly preferred.

In a preferred embodiment of C-imidazo[1,2-α]pyridin-3-yl-methylamine $R^4$ denotes $C_{1-12}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, heptyl, octyl, nonyl, decyl, undecyl, dodecyl, in each case singly or multiply substituted or unsubstituted, branched or unbranched, or in each case optionally singly or multiply substituted or unsubstituted, branched or unbranched; $C_{3-8}$-cycloalkyl, in each case singly or multiply substituted or unsubstituted, singly unsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted or unsubstituted; or a radical according to formula II

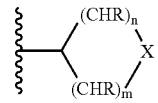

wherein in each case
n denotes a number between 0 and 6,
m denotes a number between 0 and 6,
$1 \leq m+n \leq 6$,
x denotes O, S, SO, SO or $NR^7$,
R independently of one another denotes H, F, Br, I, Cl, OH, SH, $NH_2$, $NO_2$, $CH_3$, $C_2H_5$, $OCH_3$, $OC_2H_5$, $OCF_3$.

In a preferred embodiment of C-imidazo[1,2-α]pyridin-3-yl-methylamine $R^3$ denotes $C_{1-6}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched; $C_{3-8}$-cycloalkyl, in each case singly or multiply substituted or unsubstituted, singly unsaturated or unsaturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted or unsubstituted; or aryl or heteroaryl, in each case substituted or unsubstituted; or $COOR^{10}$.

In a preferred embodiment of C-imidazo[1,2-α]pyridin-3-yl-methylamine $R^1$ denotes $C_2H_5$, $CH_3$, $CF_3$ or Cl, in particular $CH_3$, $CF_3$ or Cl, preferably $CH_3$.

In a preferred embodiment of C-imidazo[1,2-α]pyridin-3-yl-methylamine $R^5$ denotes H; $C_{1-6}$-alkyl, singly or multiply substituted or unsubstituted, saturated or unsaturated, branched or unbranched; or methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched.

In a preferred embodiment of C-imidazo[1,2-α]pyridin-3-yl-methylamine $R^3$ denotes H; $C_{1-6}$-alkyl, singly or multiply substituted or unsubstituted, saturated or unsaturated, branched or unbranched; or methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched;

preferably denotes $C_{1-6}$-alkyl, singly or multiply substituted or unsubstituted, saturated or unsaturated, branched or unbranched; or methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched.

In a preferred embodiment of C-imidazo[1,2-α]pyridin-3-yl-methylamine $R^2$ denotes H.

In a preferred embodiment consisting of C-imidazo[1,2-α]pyridin-3-yl-methylamine $R^6$ denotes H; $C_{1-6}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched.

In a preferred embodiment of C-imidazo[1,2-α]pyridin-3-yl-methylamine the radicals $R^5$ and $R^6$ together form a ring and denote $CH_2CH_2OCH_2CH_2$, $CH_2CH_2NR^{11}CH_2CH_2$ or $(CH_2)_{3-6}$.

The preparation of the substituted C-imidazo[1,2-α]pyridin-3-yl-methylamines of the general formula I may be carried out according to conventional methods known to the person skilled in the art.

The preparation of the compounds according to the invention of the general formula I is preferably carried out stepwise, in a first step by reacting a substituted 2-aminopyridine of the general formula III, wherein $R^1$ and $R^2$ have the meanings according to the general formula I given above,

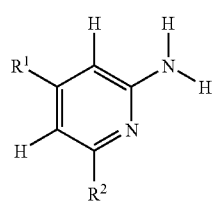

preferably in solution, with an α-halogencarbonyl compound of the general formula IV,

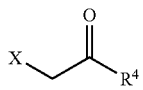

wherein the radicals $R^3$ and $R^4$ have the meanings according to the general formula I and X denotes halogen, preferably Cl, Br or I, with the splitting off of water and hydrogen halide and formation of the intermediate of the formula V

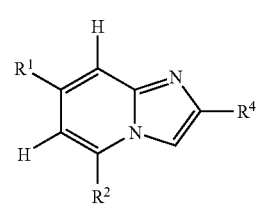

followed by aminomethylation of this intermediate V in a second step.

Advantageously the first process step is carried out under conditions in which water and/or hydrogen halide are preferably continuously removed from the reaction mixture.

Hydrogen halide may be bound preferably by adding soluble or insoluble organic or inorganic bases and thereby removed from the reaction mixture. Water can be removed from the reaction mixture preferably by azeotropic distillation or by addition of drying agents or hygroscopic substances.

The preparation of the intermediates according to the invention of the general formula V according to the above process, with or without solvents, at temperatures of more than 100° C., represents a further possible way of removing water from the reaction mixture.

Particularly preferably the preparation of the intermediates according to the invention of the general formula V is carried out by reacting substituted 2-aminopyridines of the general formula III with α-halogencarbonyl compounds of the general formula IV, wherein X denotes Br, in boiling, anhydrous ethanol.

Also preferred is the preparation of the intermediates according to the invention of the general formula V by reacting substituted 2-aminopyridines of the general formula III with α-halogencarbonyl compounds of the general formula IV, wherein X denotes Br or Cl, in boiling, anhydrous dichloromethane and/or trichloromethane in a water separator.

The substituted 2-aminopyridines of the general formula III as well as the α-halogencarbonyl compounds of the general formula IV are generally available on the market or can be prepared by conventional methods known to the person skilled in the art.

The second process step is the aminomethylation of the intermediates according to the invention of the general formula V by reaction with iminium salts of the formula VI, which may be prepared separately beforehand, as well as in situ.

The iminium salt of the general formula VI,

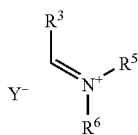

VI wherein Y preferably denotes Cl⁻, AlCl$_4^-$, Br⁻ or I⁻, may be prepared by processes known in the literature by reacting aminals of the general formula VII

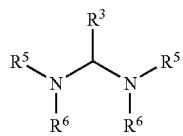

VII with acid chlorides, for example acetyl chloride or thionyl chloride (Houben-Weyl, Methoden der Organischen Chemie, E21b, 1995, pp. 1925-1929). For $R^3$=COOR$^{10}$ however, the corresponding process has been described by Merla et al. (Merla B., Grumbach H.-J., Risch N.; Synthesis 1998, 1609-1614). Both articles constitute an integral part of the description.

The iminium salts of the general formula VI do not have to be isolated, but can be reacted in situ with intermediates according to the invention of the general formula V to form substances according to the invention of the general formula I.

A suitable process for introducing a dimethylaminomethyl radical is also to react intermediates according to the invention of the general formula V with paraformaldehyde and dimethyl ammonium chloride at temperatures between 50° and 150° C.

The substituted C-imidazo[1,2-α]pyridin-3-yl-methylamines according to the invention of the general formula I may be isolated as free base or also as a salt, depending on the process used for their production. The free base of the respective compound of the general formula I is normally obtained after completed reaction according to the aforedescribed process according to the invention and optionally following working-up according to conventional methods known to the person skilled in the art. The free base of the respective compound of the general formula I that is thereby obtained or formed in situ without isolation may then be converted into the corresponding, physiologically compatible salt, for example by reaction with an inorganic or organic acid, preferably with hydrochloric acid, hydrobromic acid, sulfuric acid, phosphoric acid, methansulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid.

The conversion of the respective compound of the general formula I may preferably also be achieved by reacting the compound of the general formula I, dissolved in a suitable organic solvent such as e.g. butan-2-one (methyl ethyl ketone), as free base with trimethylsilyl chloride (TMSCl).

If the substituted C-imidazo[1,2-α]pyridin-3-yl-methylamines according to the invention of the general formula I are obtained by the preparation process according to the invention in the form of their racemates or other mixtures of their various enantiomers and/or diastereomers, these can be separated and optionally isolated by customary methods known to the person skilled in the art. By way of example there may be mentioned chromatographic separation processes, in particular liquid chromatography processes under normal pressure or under elevated pressure, preferably MPLC and HPLC processes, as well as processes involving fractional crystallisation. In this connection in particular individual enantiomers, for example diastereomeric salts formed by means of chiral phase HPLC or by means of crystallisation with chiral acids, for example (+)-tartaric acid, (−)-tartaric acid or (+)-10-camphorsulfonic acid, may be separated from one another.

The compounds are or appear to be toxicologically safe.

The present invention accordingly also provides a pharmaceutical formulation containing at least one substituted C-imidazo[1,2-α]pyridin-3-yl-methylamine according to the invention or a substituted C-imidazo[1,2-α]pyridin-3-yl-methylamine according to the general formula I given above, as well as optionally auxiliary substances and/or further adjuvants.

The present invention furthermore also provides for the use of at least one substituted C-imidazo[1,2-α]pyridin-3-yl-methylamine according to the invention or a substituted C-imidazo[1,2-α]pyridin-3-yl-methylamine according to the general formula I given above—optionally as inhibitor of nitrogen monoxide synthase—for the preparation of a pharmaceutical formulation for treating migraine, sceptic shock, neurodegenerative diseases such as multiple sclerosis, Parkinson's disease, Alzheimer's disease or Huntington's disease, inflammation pain, cerebral ischemia, diabetes, meningitis, arteriosclerosis, cancers or for wound healing.

The corresponding pharmaceutical formulations may be present as liquid, semi-solid or solid medicinal forms, for example in the form of injection solutions, drops, juices, syrups, sprays, suspensions, granules, tablets, patches, capsules, plasters, suppositories, ointments, creams, lotions, gels, emulsions, aerosols or in multiparticulate form, for example in the form of pellets or granules, and may also be administered as such.

In addition to at least one substituted C-imidazo[1,2-α]pyridin-3-yl-methylamine according to the invention of the general formula I, the pharmaceutical formulations according to the invention normally contain further physiologically compatible pharmaceutical auxiliary substances, which are preferably selected from the group comprising carrier materials, fillers, solvents, diluents, surfactants, colourants, preservatives, disintegrants, intestinal lubricants, lubricants, aroma substances and binders.

The choice of the physiologically compatible auxiliary substances as well as the amounts thereof to be used depend on whether the pharmaceutical formulation is to be applied orally, subcutaneously, parenterally, intravenously, intraperitoneally, intradermally, intramuscularly, intranasally, buccally, rectally or topically, for example to infections of the skin, mucous membranes and eyes. For oral application preparations in the form of tablets, sugar-coated pills, capsules, granules, pellets, drops, juices and syrups are preferred, while for parenteral, topical and inhalative application solutions, suspensions, readily reconstitutable dry preparations as well as sprays are suitable. Compounds according to the invention of the general formula I in depôt form, in dissolved form or in a plaster, optionally with the addition of agents promoting penetration of the skin, are suitable percutaneous application preparations. Orally or percutaneously applicable preparation forms may also provide for the delayed release of the compounds according to the invention of the general formula I.

The pharmaceutical formulations are produced with the aid of conventional means, equipment, methods and processes known to the person skilled in the art, such as are described for example in "Remington's Pharmaceutical Sciences", Ed. A. R. Gennaro, 17$^{th}$ Edition, Mack Publishing Company, Easton, Pa. (1985), in particular in Part 8, Chapters 76 to 93. The corresponding literature description is introduced here by way of reference and thus constitutes part of the disclosure.

The amount of the respective compound of the general formula I to be administered to the patient may vary and depends for example on the weight or age of the patient as well as on the mode of application, medical indications and severity of the disease. Normally 0.1 to 5000 mg/kg, preferably 1 to 500 mg/kg, particularly preferably 2 to 250 mg per kg body weight of the patient of at least one compound of the general formula I is/are applied.

The following examples are provided for purposes of further description of certain embodiments of the invention and are not, nor should they be interpreted to be, limiting.

EXAMPLES

Example 1

Synthesis of 2,7-dimethylimidazo[1,2-α]pyridin-3-ylmethyl)-dimethylamine

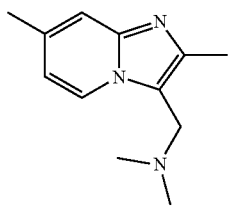

1.50 g of 2,7-dimethylimidazo[1,2-α]pyridine were added at 0° C. under a nitrogen atmosphere to 0.83 g of formaldehyde (37% formalin) and 1.30 ml of dimethylamine (40% in water) in 1.41 ml of glacial acetic acid, and the reaction mixture was heated for 2 hours at 50° C. and stirred overnight at a temperature of 20° to 25° C. For the purpose of further purification the reaction mixture was made alkaline with 10% sodium hydroxide and extracted with diethyl ether. The organic phases were combined and dried over sodium sulfate. 1.70 g of the crude product were obtained after removing the organic solvent by distillation. After purification by column chromatography 177 mg of the product were obtained as a colourless oil. 177 mg of the base were diluted with 1 ml of ethyl methyl ketone, and precipitated as hydrochloride by addition of 0.009 ml of water and 0.121 ml of chlorotrimethylsilane, followed by stirring overnight. 170 mg of 2,7-dimethylimidazo[1,2-α]pyridin-3-ylmethyl)-dimethylamine hydrochloride (corresponding to 6.5% of the theoretical amount) were obtained as a colourless solid.

Example 2

Molecular Pharmacology Investigation

The IC50 value of the compound of the example was determine in a citrullin assay. This assay was carried out as described by D. S. Bredt and S. H. Snyder (Proc. Natl. Acad. Sci. USA (1990), 87, 682-685). The results of the compound of the example in the citrullin assay are shown in Table 1.

TABLE 1

| Compound No. | Inhibition of Nitrogen Monoxide Synthase IC 50 [μm] |
|---|---|
| 1 | 4.0 |

What is claimed is:
1. A substituted C-imidazo[1,2-α]pyridin-3-yl-methylamine compound corresponding to formula I,

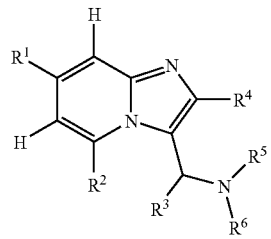

wherein,
$R^1$ denotes OH, SH, $NH_2$, $NHCH_3$, $N(CH_3)_2$, $CH_3$, $CH_2Cl$, $CH_2F$, $CHF_2$, $CF_3$, $OCH_3$, $OCH_2Cl$, $OCH_2F$, $OCHF_2$, $OCF_3$, $SCH_3$, $SCF_3$, $C_2H_5$, $CHClCH_3$, $CH_2CH_2Cl$, $CHFCH_3$, $CH_2CH_2F$, $CH_2CHF_2$, $CH_2CF_3$, $OC_2H_5$, COOH, $CH_2OH$, $CHOHCH_3$, $CH_2CH_2OH$, CN, $NO_2$, F, Br, I or Cl, $R^2$ denotes H or $CH_3$, $R^3$ denotes H; $C_{1-6}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched; $C_{3-8}$-cycloalkyl, in each case singly or multiply substituted or unsubstituted, singly unsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted or unsubstituted; or aryl or heteroaryl, in each case substituted or unsubstituted; or $COOR^{10}$, $R^4$ denotes H; $C_{1-12}$-alkyl, singly or multiply substituted with F, Cl, Br, I, $NH_2$, SH, or OH or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, heptyl, octyl, nonyl, decyl, undecyl, dodecyl, in each case singly or multiply substituted with F, Cl, Br, I, $NH_2$, SH, or OH or unsubstituted, branched or unbranched; $C_{3-8}$-cycloalkyl, in each case singly or multiply substituted with F, Cl, Br, I, $NH_2$, SH, or OH or unsubstituted, singly unsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted with F, Cl, Br, I, $NH_2$, SH, or OH or unsubstituted; or a radical according to formula II,

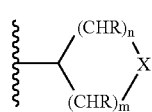

wherein, in each case,
n denotes a number between 0 and 6,
m denotes a number between 0 and 6, and $1 \leq m+n \leq 6$,
X denotes O, S, SO, $SO_2$ or $NR^7$,
R independently of one another denotes H, F, Br, I, Cl, OH, SH, $NH_2$, $NO_2$, $CH_3$, $C_2H_5$, $OCH_3$, $OC_2H_5$, $OCF_3$,
$R^5$ denotes H; $C_{1-6}$-alkyl, singly or multiply substituted with F, Cl, Br, I, $NH_2$, SH, or OH or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-ethylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted with F, Cl, Br, I, $NH_2$, SH, or OH or unsubstituted, branched or unbranched, or $C_{3-8}$-cycloalkyl, in each case optionally singly or multiply substituted with F, Cl, Br, I, $NH_2$, SH, or OH or unsubstituted, singly unsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted with F, Cl, Br, I, $NH_2$, SH, or OH or unsubstituted;
$R^6$ denotes H; $C_{1-6}$-alkyl, singly or multiply substituted with F, Cl, Br, I, $NH_2$, SH, or OH or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted with F, Cl, Br, I, $NH_2$, SH, or OH or unsubstituted, branched or unbranched, or $C_{3-8}$-cycloalkyl, in each case singly or multiply substituted with F, Cl, Br, I, $NH_2$, SH, or OH or unsubstituted, singly unsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted with F, Cl, Br, I, $NH_2$, SH, or OH or unsubstituted; or aryl, heteroaryl, $C_{1-4}$-alkyl aryl or $C_{1-4}$-alkyl heteroaryl unsubstituted or singly or multiply substituted;
or the radicals $R^5$ and $R^6$ together form a ring and denote $CH_2CH_2OCH_2CH_2$, $CH_2CH_2NR^{11}CH_2CH_2$ or $(CH_2)_{3-6}$,
$R^7$ denotes H, $C_{1-6}$-alkyl, methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, 1-ethylpropyl or hexyl, $C_{3-8}$-cycloalkyl, cyclopropyl, 2-methylcyclopropyl, cycloprophlmethyl, cyclobutyl, 2-methylcyclobutyl, 3-methylcyclobutyl, cyclobutylmethyl, cyclopentyl, cyclohexyl or cyclooctyl, acyl, $C(O)R^8$, sulfonyl or $S(O_2)R^9$,
$R^8$ denotes H, a $C_{1-6}$-alkyl radical or an aryl radical,
$R^9$ denotes H, a $C_{1-6}$-alkyl radical or an aryl radical,
$R^{10}$ denotes H, a $C_{1-6}$-alkyl radical or an aryl radical,
$R^{11}$ denotes H, $C_{1-6}$-alkyl or $C_{3-8}$-cycloalkyl, aryl or heteroaryl, aryl or heteroaryl bonded via $C_{1-3}$-alkylene, acyl $C(O)R^{12}$ or sulfonyl $S(O_2)R^{13}$,
$R^{12}$ denotes H, a $C_{1-6}$-alkyl radical or an aryl radical,
$R^{13}$ denotes H, a $C_{1-6}$-alkyl radical or an aryl radical,
or a salt thereof with a physiologically tolerated acid, provided that the compounds:

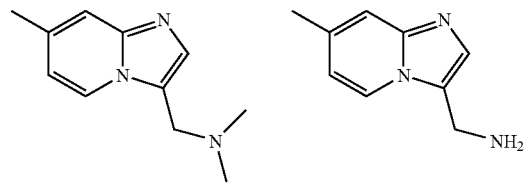

are excluded.

2. The compound of claim 1, wherein said compound is present in the form of a free base.

3. The compound of claim 1, wherein said compound contains at least one asymmetric center and is present in the form of a pure enantiomer or pure diastereoisomer.

4. The compound of claim 1, wherein said compound contains at least one asymmetric center and is present in the form of a mixture of stereoisomers.

5. The compound of claim 1, wherein said compound contains at least one asymmetric center and is present in the form of a racemic mixture.

6. A C-imidazo[1,2-α]pyridin-3-yl-methylamine compound according to claim 1, wherein $R^4$ denotes $C_{1-12}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, heptyl, octyl, nonyl, decyl, undecyl, dodecyl, in each case singly or multiply substituted or unsubstituted, branched or unbranched, or in each case optionally singly or multiply substituted or unsubstituted, branched or unbranched; $C_{3-8}$-cycloalkyl, in each case singly or multiply substituted or unsubstituted, singly unsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted or unsubstituted; or a radical according to formula II

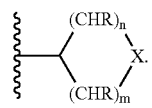

7. A C-imidazo[1,2-α]pyridin-3-yl-methylamine compound according to claim 1, wherein $R^3$ denotes $C_{1-6}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched; $C_{3-8}$-cycloalkyl, in each case singly or multiply substituted or unsubstituted, singly unsaturated or unsaturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted or unsubstituted; or aryl or heteroaryl, in each case substituted or unsubstituted; or $COOR^{10}$.

8. A C-imidazo[1,2-α]pyridin-3-yl-methylamine compound according to claim 1, wherein $R^1$ denotes $C_2H_5$, $CH_3$, $CF_3$ or Cl.

9. A C-imidazo[1,2-α]pyridin-3-yl-methylamine compound according to claim 1, wherein $R^1$ denotes $CH_3$, $CF_3$ or Cl.

10. A C-imidazo[1,2-α]pyridin-3-yl-methylamine compound according to claim 1, wherein $R^1$ denotes $CH_3$.

11. A C-imidazo[1,2-α]pyridin-3-yl-methylamine compound according to claim 1, wherein $R^5$ denotes H; $C_{1-6}$-alkyl, singly or multiply substituted or unsubstituted, saturated or unsaturated, branched or unbranched; or methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched.

12. A C-imidazo[1,2-α]pyridin-3-yl-methylamine compound according to claim 1, wherein $R^3$ denotes H; $C_{1-6}$-alkyl, singly or multiply substituted or unsubstituted, saturated or unsaturated, branched or unbranched; or methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched.

13. A C-imidazo[1,2-α]pyridin-3-yl-methylamine compound according to claim 1, wherein $R^3$ denotes $C_{1-6}$-alkyl, singly or multiply substituted or unsubstituted, saturated or unsaturated, branched or unbranched; or methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched.

14. A C-imidazo[1,2-α]pyridin-3-yl-methylamine compound according to claim 1, wherein $R^2$ denotes H.

15. A C-imidazo[1,2-α]pyridin-3-yl-methylamine compound according to claim 1, wherein $R^6$ denotes H; $C_{1-6}$-alkyl, singly or multiply substituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert.-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case singly or multiply substituted or unsubstituted, branched or unbranched, or in each case optionally singly or multiply substituted or unsubstituted, branched or unbranched.

16. A C-imidazo[1,2-α]pyridin-3-yl-methylamine compound according to claim 1, wherein the radicals $R^5$ and $R^6$ together form a ring and denote $CH_2CH_2OCH_2CH_2$, $CH_2CH_2NR^{11}CH_2CH_2$ or $(CH_2)_{3-6}$.

17. A pharmaceutical formulation comprising at least one C-imidazo[1,2-α]pyridin-3-yl-methylamine compound according to claim 1 and at least one auxiliary substance.

18. A method of treating migraine, said method comprising the step of administering to a subject in need thereof a pharmaceutically effective amount of a compound according to claim 1.

* * * * *